United States Patent [19]

Fuller

[11] 4,209,457

[45] Jun. 24, 1980

[54] PRODUCTION OF HALOGENATED BENZONITRILES

[75] Inventor: George Fuller, Bristol, England

[73] Assignee: I.S. C. Chemicals Limited, London, England

[21] Appl. No.: 7,596

[22] Filed: Jan. 29, 1979

[30] Foreign Application Priority Data

Jan. 28, 1978 [GB] United Kingdom ................. 3576/78

[51] Int. Cl.² ........................................... C07C 121/52
[52] U.S. Cl. ............................................... 260/465 G
[58] Field of Search .................................... 260/465 G

[56] References Cited

U.S. PATENT DOCUMENTS 3,290,353 12/1966 Battershell et al. .................. 260/465

Primary Examiner—Dolph H. Torrence
Attorney, Agent, or Firm—Holman & Stern

[57] ABSTRACT

A process for the production of a fluorobenzonitrile wherein a chlorobenzonitrile having a chlorine atom in an ortho- or para- position with respect to a nitrile group is heated with an alkali metal fluoride at a temperature between 200° and 250° C., in the presence of sulpholane.

8 Claims, No Drawings

PRODUCTION OF HALOGENATED BENZONITRILES

This invention relates to the production of halogenated benzonitriles, and more particularly to the production of fluorobenzonitriles containing at least one nitrile group and at least one fluorine atom attached to ring carbon atoms, the fluorine atoms being in ortho and/or para-positions with respect to the nitrile group.

Fluorobenzonitriles are in demand as intermediates in the production of physiologically-active compounds such as those sold under the trade-names "Floxacillin", "Flurazepam" and "Difluron" (Registered Trade Marks).

It is known to produce fluorobenzonitriles by halogen-exchange reactions in which chlorobenzonitriles are heated with dry alkali metal fluoride in aprotic solvents, such a dimethyl sulphone and dimethyl formamide.

However, the use of these solvents is usually restricted to temperatures of 230° C. or below and consequently long reaction times have been required to produce acceptably-high yields of the fluorobenzonitrile product. For example 2-chlorobenzonitrile when heated for 40 hours at 200° C. with KF in dimethyl sulphone as solvent gave a 66.5% yield of 2-fluorobenzonitrile (see Chemical Communications No. 18, Sept. 22, 1965, page 430).

Solvents used in the prior art, e.g. dimethyl formamide (b.p. 153° C.) or dimethyl sulphone (b.p. 230° C.), have similar boiling points to either the starting materials or the products, and therefore solvent recovery is difficult to carry out economically.

This invention consists in a process for the production of a fluorobenzonitrile wherein a chlorobenzonitrile having a chlorine atom in an ortho- or para- position with respect to a nitrile group is heated with an alkali metal fluoride at a temperature between 200° and 250° C., in the presence of sulpholane.

Preferably the alkali metal fluoride is potassium fluoride.

Preferably the temperature of reaction is between 210° and 240° C.

Preferably the mole ratio of sulpholane: chlorobenzonitrile in the reaction mixture is between 1:1 and 6:1.

Preferably the reaction is conducted with stirring and under slight reflux of the product if necessary. A preferred reaction time is between 6 and 12 hours.

Normally the reaction will be carried out at atmospheric pressure.

It is to be understood that the starting material may contain one, two or more chlorine atoms per molecule. Where it contains two or more chlorine atoms it is within the scope of the invention to replace only part of the chlorine content by fluorine, although total substitution of chlorine by fluorine is possible. Preferred starting materials are 2-chlorobenzonitrile and 2,6-dichlorobenzonitrile, although 4-chlorobenzonitrile may also be fluorinated by the method of the invention.

There are two main advantages in using sulpholane in the method according to the invention. The first advantage is that it is an effective stable solvent for the reactants at 210°–240° C., and the products derived from the reaction are substantially free of impurities (other than starting material). Secondly, because of its high boiling point (287°/760 mm), it is very easy to recover the solvent for re-use, for example by flash-distillation of all the organics from the residual potassium salts, e.g. in a paddle dryer or pan dryer, and recovering the desired lower-boiling benzonitriles by fractional distillation from the condensate and returning the solvent to the reaction vessel. This fractional distillation will normally be carried out under a reduced pressure, e.g. 30 to 100 mm Hg absolute.

Alternatively the products of the reaction may be isolated by steam-distillation of the reaction mixture at the end of the reaction period, with solvent extraction of the organic products from the steam distillate and fractional distillation of the organic extract.

The invention will be further described with reference to the following non-limiting examples. Example 1 relates to the preparation of 2,6-difluorobenzonitrile from the 2,6-dichloro- compound, Example 2 to the preparation of the 2-chloro, 6-fluoro- compound, Example 3 to the preparation of 2-fluorobenzonitrile and Example 4 to the preparation of the 4-fluorobenzonitrile.

EXAMPLE 1

In the first run, a mixture of 2,6-dichlorobenzonitrile (258.1 g., 1.5 moles) and anhydrous potassium fluoride (192.4 g., 3.3 moles) in sulpholane (501 g., 4.2 moles) was stirred at 210°–215° for 6 hr. in a 2-liter flanged flask fitted with a stainless steel stirrer, thermometer pocket and single surface reflux condenser. Analysis by g.l.c. at this stage showed the presence of 17.5% of 2,6-difluorobenzonitrile, 16.4% of 2-chloro-6-fluorobenzonitrile, 2.3% of 2,6 dichlorobenzonitrile and 63.5% sulpholane. The mixture was then heated further at 215° for 2 hr. and at 235° for 5 hr., after which further analysis showed the presence of 31.0% of 2,6-difluorobenzonitrile, 1.7% of 2-chloro-6-fluorobenzonitrile and 67% sulpholane. Water (500 c.c.) was then added to the cold reaction mixture which was steam distilled until about 3 l. of distillate and white crystals had been collected. Methylene chloride (200 c.c.) was added in order to collect the organic phase as a liquid. It was combined with the organic product of a second fluorination run below.

In the second run, a mixture of 2,6-dichlorobenzonitrile (258.5 g., 1.5 moles), anhydrous potassium fluoride (189.0 g., 3.3 moles), and sulpholane (508.0 g., 4.2 moles) was stirred at 235° for 9 hr. to give 2,6-difluorobenzonitrile (33.3%), 2-chloro-6-fluorobenzonitrile (4.6%), and sulpholane (61.8%). The organic product was isolated as in the previous run.

The combined organic product from the two runs was fractionally distilled from a 500 c.c 3-necked flask through a vacuum-jacketed column (35 cm×1.8 c.m diameter) packed with 2.6×1.6 mm stainless steel Dixon gauzes. The methylene chloride was first distilled off at atmospheric pressure at a 1 in 5 take-off ratio. Further distillation at reduced pressure gave (i) a fore-run (1.9 g.), b.p. 84°–96°/32 mm., (ii) 2,6-difluorobenzonitrile (231.9 g., 99.9% purity by g.l.c.), b.p. 102°–114°/30–33 mm, m.p. 30°, and (iii) a pot residue (45.9 g.) containing a mixture of 30% 2,6-difluorobenzonitrile and 64% 2-chloro-6-fluorobenzonitrile.

The combined input of 2,6-dichlorobenzonitrile from the two runs was 516.6 g. (3.0 moles). The product isolated was 2,6-difluorobenzonitrile (245.6 g., 1.77 moles) in 59% conversion, and 2-chloro-6-fluorobenzonitrile (29.3 g. 0.19 moles) in 6.3% conversion, an overall carbon recovery of 65.3%.

EXAMPLE 2

The same equipment was used as in Example 1. In the first run a mixture of 2,6-dichlorobenzonitrile (344.0 g., 2.0 moles), anhydrous potassium fluoride (127.6 g., 2.2 moles), and sulpholane(501.1 g., 4.2 moles) was stirred at 210°/215° for 10 hr. Water (500 c.c.) was then added to the cold reaction mixture which was steam distilled until about 7 l. of distillate has been collected. Most of the water was then decanted from the white solid and enough methylene chloride (350 c.c.) added to dissolve the solid. A second run was carried out on a further 344 g. (2 moles) of 2,6-dichlorobenzonitrile under identical conditions.

The product from the two runs was combined and the methylene chloride was distilled off at atmospheric pressure through the fractionating column at a 1 in 5 take-off ratio. The residue (395.6 g) was distilled in a 1 in 5 take-off ratio to give (i) a fore-run (3.8 g.), b.p. 30°-94°/32 mm, (ii) 2,6-difluorobenzonitrile (71.9 g), b.p. 94°-102°/32 mm, (iii) an intermediate cut (17.3 g), b.p. 102°-104°/32 mm, (iv) 2-chloro-6-fluorobenzonitrile (218.8 g.), b.p. 118° (approx.)/20 mm., m.p. 58.5°-59°, and (v) a residue, mainly 2,6-dichlorobenzonitrile (128.1 g.).

An accurate boiling point of the chlorofluorobenzonitrile could not be obtained because of the need to heat the take-off lines with infra-red lamps to prevent solidification.

The overall result from the combined double run was a 13% conversion into 2,6-difluorobenzonitrile, a 35.3% conversion into 2-chloro-6-fluorobenzonitrile, and about 19% unchanged 2,6-dichlorobenzonitrile was present. The carbon recovery was therefore 66.7%

EXAMPLE 3

A mixture of 2-chlorobenzonitrile, m.p. 93°, (200 g., 1.45 moles) and KF (99.9 g., 1.72 moles) in sulpholane (720 g., 5.85 moles) was kept at 240° for 20 hr. (slight reflux) in a 2 l. flanged flask fitted with a stainless steel stirrer, thermometer pocket and reflux condenser. The conversion of 2-chlorobenzonitrile (2ClBN) into 2-fluorobenzonitrile (2FBN) was 48% after the first 9 hr. and 77% after a total reaction time of 20 hr., according to g.l.c. analysis. Water (700 c.c.) was then added to the cold reaction mixture which was then steam distilled to give a mixture of 2FBN and 2 ClBN (148.3 g) and water(6.5 l.). The benzonitriles therefore are steam distilled in about 2% w/w of the total distillate. A further 2 l. of steam distillate was then collected, after which no more organics were observed.

The organic layer from the two distillates was combined after the addition of about 50 c.c. of methylene chloride to dissolve up a small quantity of solid in the second distillate.

The above product was combined with the product of a second run, using further 2ClBN (200.8 g., 1.46 moles), KF (100.4 g., 1.73 moles) and sulpholane (718 g., 5.98 moles) at 240° for 22 hr. and steam distilled as before.

The combined product was fractionally distilled through a 35×1.8 cm vacuum-jacketed column packed with 1.6×1.6 mm Dixon gauzes. The methylene chloride was first removed at atmospheric pressure, and the distillation was then continued under reduced pressure at a take-off ratio of 1 in 5 to give (i) 2-fluorobenzonitrile (178.5 g.), b.p. 94°-98°/30 mm., a colourless liquid, 99.9% purity by g.l.c., and (ii) a solid pot residue (91.1 g) containing a mixture of 25.2% 2FBN and 73.7% 2-chlorobenzonitrile.

From an input of 400.8 g. (2.91 moles) of 2ClBN there was obtained 201.5 g. (1.66 moles) of 2FBN (including the 2FBN content of the residue), i.e. 57% conversion, and 67.1 g (16.7%) of unchanged 2ClBN, a total carbon recovery of 73.7%.

EXAMPLE 4

A mixture of 4-chlorobenzonitrile (13.7 g., 0.1 mole) and potassium fluoride (11.6 g., 0.2 moles) in sulpholane (102 g., 0.85 moles) was stirred at 238°-240° for 21 hours in a 250 c.c. 3 necked flask fitted with a p.t.f.e. blade stirrer, thermometer pocket and reflux condenser.

The cold reaction slurry was then transferred into a rotary film evaporator flask of 500 c.c. capacity and the volatile organic portion was distilled under reduced pressure to give
(i) Fraction 1 (86.4 g.), b.p. 178°-208° C. (oil bath temperature) at 35 mm., and (ii) Fraction 2 (11.1 g), b.p. 166°-208° (oil bath temperature) at 5 mm.

The above two fractions were combined (97.5 g.) and were analysed by gas-liquid chromatography on a 5 ft Carbonax 20 M (10%) on 100/200 mesh Gas Chrom Q and found to contain 6.27% of 4-fluorobenzonitrile, 1.78% of 4-chlorobenzonitrile, and 91.92% of sulpholane (calibrated result).

The g.l.c. result showed that 4-fluorobenzonitrile (6.1 g.) was formed in 50.4% conversion, with recovered 4-chlorobenzonitrile (1.7 g) as 12.4% of input. Sulpholane (89.6 g) was recovered as 88% of input.

I claim:

1. A process for the production of a fluorobenzonitrile comprising heating a chlorobenzonitrile having a chlorine atom in a position selected from the ortho- and para-positions with respect to a nitrile group with potassium fluoride at a temperature between 200° and 250° C. in the presence of sulpholane the molar ratio of sulpholane to chlorobenzonitrile in the reaction mixture being between 1:1 and 6:1 and separating the sulpholane from the reactions products by distillation.

2. The process according to claim 1, wherein the reaction temperature is between 210° and 240° C.

3. The process according to claim 1 comprising carrying out the reaction under reflux at atmospheric pressure.

4. The process according to claim 1, wherein the reaction period is from 6 to 12 hours.

5. The process according to claim 1, wherein the chlorobenzonitrile contains one chlorine atom per molecule.

6. The process according to claim 5, wherein the chlorobenzonitrile is 2-chlorobenzonitrile.

7. The process according to claim 1, wherein the chlorobenzonitrile contains two chlorine atoms per molecule.

8. The process according to claim 7, wherein the chlorobenzonitrile is 2,6-dichlorobenzonitrile.

* * * * *